United States Patent [19]

Nelson

[11] Patent Number: 4,502,562
[45] Date of Patent: Mar. 5, 1985

[54] STETHOSCOPE WITH REMOVABLE INSERT

[75] Inventor: Carl T. Nelson, North St. Paul, Minn.

[73] Assignee: Minnesota Mining and Manufacturing Company, St. Paul, Minn.

[21] Appl. No.: 479,158

[22] Filed: Mar. 28, 1983

[51] Int. Cl.³ .............................................. A61B 7/02
[52] U.S. Cl. ...................... 181/131; 181/137
[58] Field of Search ............... 181/137, 131, 129, 135

[56] References Cited

U.S. PATENT DOCUMENTS

| 1,143,791 | 6/1915 | Singer. | |
|---|---|---|---|
| 1,321,266 | 11/1919 | Wilkinson | 181/131 |
| 3,108,652 | 10/1963 | Littmann | 181/24 |
| 3,152,659 | 10/1964 | Littmann | 181/24 |
| 3,215,224 | 11/1965 | Machlup | 181/24 |
| 3,223,195 | 12/1965 | Allen | 181/24 |
| 3,224,526 | 12/1965 | Weber | 181/24 |
| 3,276,536 | 10/1966 | Littmann | 181/24 |
| 3,303,903 | 2/1967 | Speelman | 181/24 |
| 3,366,198 | 1/1968 | Littmann | 181/24 |
| 3,515,239 | 6/1970 | Machlup et al. | 181/24 |

Primary Examiner—L. T. Hix
Assistant Examiner—Brian W. Brown
Attorney, Agent, or Firm—Donald M. Sell; James A. Smith; Robert W. Hoke, II

[57] ABSTRACT

A stethoscope including a bell and a removable insert therefore to better accomodate dimunitive skin areas. The insert is made of a resilient and deformable material. The insert snaps into the bell to releasably lock the insert into the bell. The insert reduces the opening to and the volume of the bell.

12 Claims, 7 Drawing Figures

STETHOSCOPE WITH REMOVABLE INSERT

BACKGROUND OF THE INVENTION

The present invention relates to stethoscopes. More particularly, it relates to stethoscopes in which the bell may be reduced in diameter to better accomodate diminutive skin areas.

The chest piece of most medical stethescopes are of the so-called dual-head type having opposed diaphragm and open bell sides which are adapted for detecting high frequency and low frequency sounds, respectively. Dual-head stethoscopes of this type are described, for example, in U.S. Pat. Nos. 3,108,652; 3,152,659; 3,215,224; 3,224,526; 3,276,536; 3,303,903; 3,366,198; and 3,515,239.

Problems are frequently encountered when the bell side of conventional stethoscope chest pieces are used on pediatric patients or on skin areas of high curvature. In such cases, it is many times difficult to acoustically seal the rim of the open bell with the underlying skin.

U.S. Pat. No. 3,223,195 discloses a stethoscope head construction comprising a double ended receiver having a large bell at one end, a small bell at its distal end and a core which is shiftable to successfully implement the operative condition of either of these bells. The large bell is said to be intended for low frequency range reception of sound, and the small bell is intended for high amplitude low frequency sound reception. The small bell also is described as suitable for use on "bony" type chests and in pediatrics and for listening to small localized areas of a chest. The stethoscope head construction is relatively complicated and not believed to conveniently adapt a conventional stethoscope chest piece for use on pediatric patients and areas of high curvature.

SUMMARY OF THE INVENTION

According to the invention, there is provided a simple stethoscope head construction accomodating a removable, resilient insert for greater flexibility and ease of useage. The stethoscope head comprises a body having a bore therein, a belt side connected to the body and having a central aperture therein opening into the bore in the body, a continuous peripheral rim connected to the bell and a resilient, deformable, generally bell-shaped insert capable of being placed within the volume of the bell such that an aperture in the insert is axially aligned with the aperture in the bell. The insert is releasably locked within the volume of the bell to facilitate its use when called for in the medical practitioner's judgment.

The removable insert is used in a conventional bell to substantially reduce the diameter of the bell and to facilitate the use of the stethoscope on diminutive chests and other body areas. By reducing the diameter of the bell, sound leakage from under the edge of the bell may be effectively eliminated on small areas or areas of high curvature. At the same time, the sound reception of the bell at the frequencies used in diagnostic auscultation may be improved by reducing the volume of the bell. The stethoscope head is simple and may be used in a wide range of diagnostic environments. It may be used on adults and quickly and easily converted for use on a child or newborn infant. A further advantage of the stethoscope of the invention is that it utilizes a removable insert of a non-metallic material to avoid the uncomfortable chill accompanying the use of a conventional steel or other metal stethoscope. The insert may be quickly and easily removed for cleaning.

Other objects and advantages of the invention will become more apparent from the following drawings wherein like numerals refer to like parts, the accompanying description and the appended claims.

DESCRIPTION OF THE PREFERRED EMBODIMENT

Figure 1:
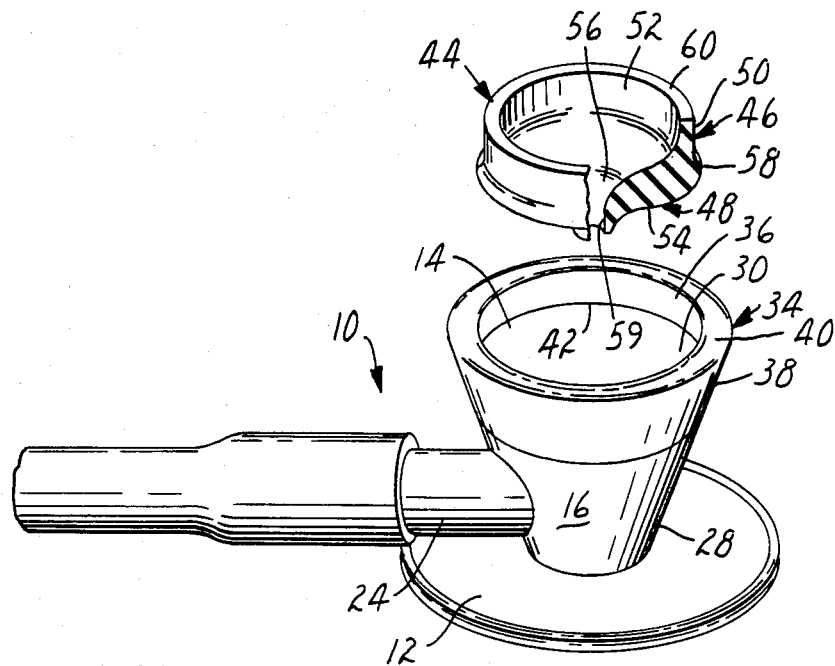
FIG. 1 is an elevated and exploded perspective view of a stethoscope head with a removable insert with portions broken away.

Referring to FIGS. 1-4, wherein like reference characters designate like parts throughout the several views, a stethoscope head 10 is shown with a conventional diaphragm 12 in back-to-back relation with an open bell 14 separated by an intermediate body portion 16. At the apex of diaphragm 12 and bell 14 are aligned apertures 18 and 20, respectfully, leading to a bore 22 through body 16. Apertures 18 and 20 are aligned substantially perpendicular to bore 22.

Body 16 is fitted with a conventional tubular stem 24. Stem 24 is, in turn, conventionally adapted to rotate within and relative to body portion 16 and has conventional aligning means to align at least the opening (not shown) in stem 24 with either aperture 18 or 20 to provide a sound passageway from the selected and properly aligned bell 14 or diaphragm 12 to stem 24. Stem 24 is adapted to be connected to a conventional binaural head set (not shown). The specific stethoscope head construction may vary greatly in accordance with known practice and may in some cases comprise a single bell rather than a dual-head construction such as that illustrated.

The bell 14 has a continuous peripheral rim 26. Rim 26 lies in a plane spaced outwardly from and at all places equidistant from the central aperture 20. This rim is continuous with an outer annular wall 28 and an inner annular wall 30. Outer annular wall 28 includes a notch 32. The inner wall 30 of bell 14 is bell shaped with its outer extremities approaching a parallel with outer wall 28. The extreme outer edge of bell 14 is narrow in diameter and tapered from a wider base to a curved edge as illustrated.

An annular cover 34 covers the rim 26 of bell 14. Cover 34 is preferably formed of an annular, flexible, resilient material. It may be formed of a neoprene or other synthetic rubber material which may be stretched or distorted to be snapped over the rim 26. The cover 34 is formed with opposed and spaced apart annular side walls 36 and 38. Outer side wall 38 is slightly longer than inner side wall 36 and terminates at notch 32. Annular- side walls 36 and 38 are interconnected by an annular web 40 and are relatively thick to provide the cushioning cover 34 over rim 26. Web 40 is integral with side walls 36 and 38 and forms the top of cover 34. Side walls 36 and 38 engage the inner side wall 30 and the outer sidewall 28 respectively of bell 14 adjacent rim 26 to hold cover 34 in place. Side wall 36 terminates at lip 42.

Cover 34 provides a resilient continuous edge adapted to be deformed to conform with the body of the patient against whom it is pressed. The deformation is a continuous and gentle one so that the overall shape of the bell 14 is not significantly changed while at the same time leakage from under the edge of the bell 14 is effectively eliminated.

Adapted for insertion into bell 14 is resilient and compliant insert 44. Insert 44 is comprised of a substantially cylindrical portion 46 and a substantially bell shaped portion 48. Cylindrical portion 46 has an outer wall 50 and an inner wall 52. Similarly bell shaped portion 48 has an outer wall 54 and an inner wall 56.

Figure 2:
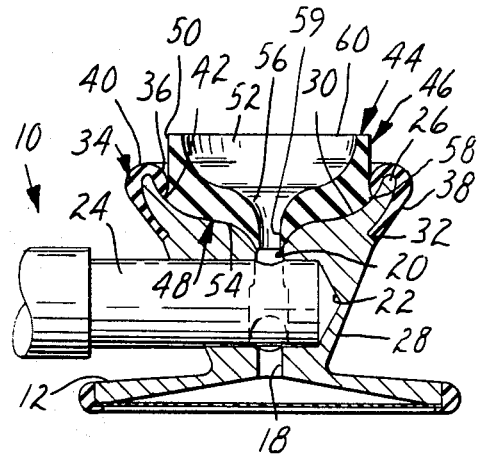
FIG. 2 is a transverse, cross-sectional view of the stethoscope head of FIG. 1.
Figure 4:
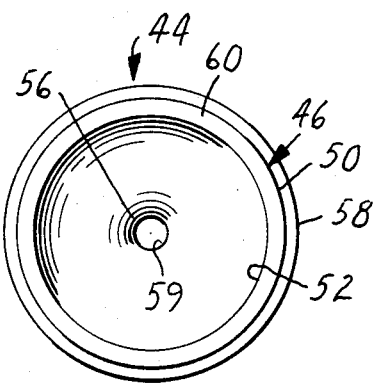
FIG. 4 is a top view of the removable insert shown in FIG. 1.
Figure 3:
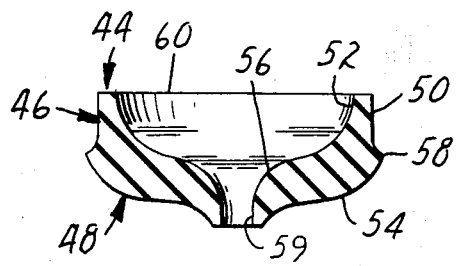
FIG. 3 is a transverse, cross-sectional view of the removable insert shown in FIGS. 1 and 2.

Outer wall 50 curves outwardly at its juncture with outer wall 54 to form a ridge 58. Outer walls 50 and 54 conform to and substantially follow the curvature and shape of the inner surface of bell 14. This is best seen in FIG. 2. Ridge 58 fits snugly into lip 42 formed by the juncture of the edge of covering 34 at inner side wall 36 with inner annular wall 30 of bell 14.

Cylindrical portion 46 extends above peripheral rim 26 to contact the skin of the patient and to allow for easy insertion and removal of insert 44 from bell 14. More particularly, because of the resilient composition of insert 44, it may be conveniently snapped in and out by merely grasping cylindrical portion 46 by hand. This allows for easy useage and simultaneously eliminates the need for an additional bell or mechanical alteration of the existing bell.

The inner contour of insert 44, as defined by inner walls 52 and 56, substantially forms a bell shape. Inner wall 56 terminates at central aperture 59 to allow soundwaves picked up on a patient's chest or other body parts to be communicated to aperture 20. Ridge 58 follows the inner contour of bell 14 and nestles tightly against covering 34 at lip 42 to hold insert 44 in place within the bell microphone 14. The region between outer wall 50 and ridge 58 is curved to follow the contour of the exposed surface of inner side wall 36 of covering 34. Similarly, the region between outer wall 54 and ridge 58 is convex in shape to follow the concave shape dictated by the inner wall of bell 14. The lower regions of bell shaped portion 48, as it approaches aperture 20, are tapered or feathered to merge into aperture 20. Hence, the diameter of aperture 20 as best shown in FIG. 2 is not significantly affected by the insertion of insert 44 into bell 14.

Stethoscope head 10 is used by contacting head 10 with the patient's skin in a manner well-known in the art. This is the same whether or not insert 44 is used. When the doctor or other user encounters chest or other body part of sufficiently high curvature or diminutive area, insert 44 is employed. By snapping insert 44 into bell 14, the diameter of peripheral rim 26 is effectively and significantly reduced. Instead of rim 26 contacting the skin, the rim 60 of cylindrical portion 46 contacts the skin. Hence, a smaller portion of relatively flat skin area is required, reducing the likelihood that sound is either lost or interference is picked up around the periphery of the rim 60 of cylindrical portion 46. In other words, the likelihood of extraneous sounds leaking in or the sound to be monitored leaking out is significantly reduced. This has been accomplished without the need of complicated mechanical devices as used in the prior art. At the same time, the objects and advantages of the invention have been accomplished without the need for modification of the basic stethoscope device.

Figure 5:
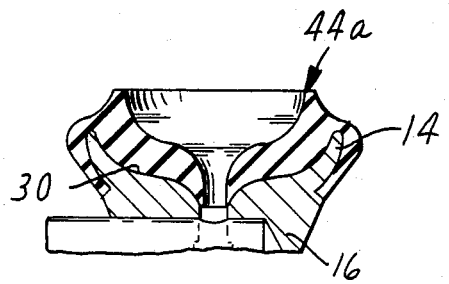
FIG. 5 is a transverse, cross-sectional view of the stethoscope head of FIG. 1 and a first alternative removable insert with portions broken away.

From the foregoing, it will be apparent that all of the objectives of this invention have been achieved by the stethoscope head and insert shown and described. It will also be apparent that various modifications and changes may be made by those skilled in the art without departing from the spirit of the invention as expressed in the accompanying claims. For example, insert 44 and cover 34 may be made into a single-piece construction as shown in FIG. 5. By combining insert 44 and cover 34 into an integral insert 44a, the shape of the underlying bell 14 may be simplified. The desired size and shape of the internal surface 30 of the bell 14 may be determined by the size and shape of the integral insert 44a. In this way, one bell may be adapted for a multiplicity of diagnostic uses through the use of a series of inserts. A relatively thinner insert may be used where a greater volume within the bell is desired. A comparatively thicker insert may be used where a smaller volume with a smaller diameter opening to the bell is desired.

It is generally preferable to decrease the volume of the bell whenever the diameter of the opening to the bell is decreased. Reducing the diameter of the bell opening reduces the total sound energy entering the bell, making it increasingly difficult for the physician or other user to detect the sound desired to be monitored. It is well known that reducing the volume of the bell increases the efficiency with which sound energy is transmitted to the sound-receiving aperture. Hence, whenever the diameter of the opening of the bell is decreased, it is generally preferable to reduce the volume of the bell simultaneously.

Figure 6:
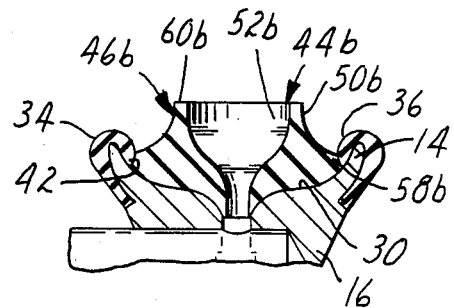
FIG. 6 is a transverse, cross-sectional view of the stethoscope head of FIG. 1 and a second alternative removable insert with portions broken away.

Rather than thickening the overall insert to reduce the volume within the bell, the portion of the insert that locks the insert within the bell needs only be thickened as shown in FIG. 6. As a result, rim 60b may be kept relatively narrow to greater insure a complete seal around the periphery of insert 44b when applied to the skin of a patient.

Rim 60b of insert 44 may be narrowed significantly by forming the outside wall 50b of cylindrical portion 46b closer to the inside wall 52b. By moving the outside wall 50b in, material is saved, a generally preferred narrow rim 60b is retained and the performance of the stethoscope head 10 is unaffected. The limit to which outside wall 50b may be drawn in is the point at which ridge 58b no longer fits snugly into lip 42. All of the outside wall 50b of portion 46b above lip 42 may be moved radially in and not contact side wall 36, assuming the material from which insert 44b is formed is sufficiently firm to hold portion 46b in the upright position even when not supported by side wall 36.

Figure 7:
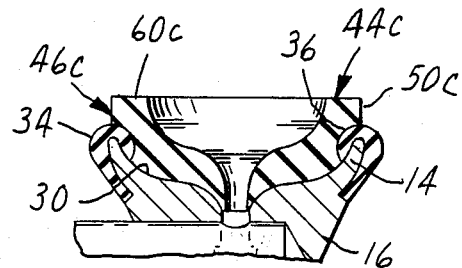
FIG. 7 is a transverse, cross-sectional view of the stethoscope head of FIG. 1 with a third alternative removable insert with portions broken away.

In the case of an insufficiently firm insert, the entire insert may be thickened as shown in FIG. 7 to afford it greater rigidity throughout. Referring to FIG. 7, an insert 44c is shown with a comparatively thicker rim 60c. Thicker rim 60c results from outside wall 50c of cylindrical portion 46c overlapping inner side wall 36 of covering 34.

Because all of these modifications and changes may be made by one skilled in the art and without departing from the spirit of the invention as expressed in the accompanying claims, all matter shown and described is to be interpreted as illustrative and not in a limiting sense.

What is claimed is:

1. A stethoscope head comprising:
   a. a body having a bore therein;
   b. a bell connected to the body and having a central aperture in the bottom thereof opening into the bore in the body and comprising (1) an inner, generally bell-shaped side wall, (2) an outer side wall and (3) a continuous peripheral rim connecting the inner side wall to the outer side wall;
   c. a resilient, deformable cover over the rim; and
   d. a resilient, deformable insert juxtaposed the inner side wall of the bell and having an aperture therein axially aligned with the aperture in the bell and including an annular ridge which engages the bell and the resilient cover to releasably lock the insert within the bell and adjacent the inner side wall of the bell.

2. The stethoscope head recited in claim 1 wherein the resilient insert includes a cylindrical portion connected to the annular ridge on the insert and having an outside diameter substantially equal to the inside diameter of the resilient cover.

3. The stethoscope head recited in claim 2 wherein the cylindrical portion of the resilient insert extends beyond the resilient cover over the rim to contact the skin area to be monitored and to facilitate removal by hand.

4. A stethoscope head comprising:
   a. a body having a bore therein;
   b. a bell connected to the body and having a central aperture therein substantially perpendicular to and opening into the bore and comprising (1) an inner, generally bell-shaped side wall, (2) an outer side wall and (3) a continuous peripheral rim formed on the bell equidistant from the bell aperture at all places and connecting the inner side wall to the outer side wall;
   c. a resilient, deformable cover over the rim reducing the inside diameter of the rim; and
   d. a one-piece, removable, resilient, deformable insert of substantially bell-shaped configuration juxtaposed the inner side wall of the bell and having a central aperture therein axially aligned with the aperture in the bell and including an annular ridge which engages the resilient cover to releasably lock the insert within the bell and adjacent the inner side wall of the bell.

5. The stethoscope recited in claim 4 wherein the insert further comprises:
   a. a cylindrical portion including a first end extending beyond the resilient cover and a second end connected to the annular ridge; and
   b. a bell-shaped portion including a first end connected to the annular ridge and a second end terminating at the aperture of the insert.

6. The stethoscope recited in claim 5 wherein the second end of the bell-shaped portion is tapered towards the aperture whereby a smooth transition is provided between the aperture of the insert and the aperture of the bell.

7. The stethoscope recited in claim 6 wherein the diameter of the aperture in the insert is substantially equal to the diameter of the aperture in the bell.

8. The stethoscope recited in claim 7 wherein the annular ridge on the insert comprises:
   a. a convex-shaped portion formed from the first end of the bell-shaped portion of the insert and contacting the inner side wall of the bell; and
   b. a concave-shaped portion formed from the second end of the cylindrical portion of the insert and contacting the rim and connected to the convex-shaped portion to form the annular ridge.

9. The stethoscope recited in claim 8 wherein the outside diameter of the cylindrical portion of the insert is substantially equal to the inside diameter of the resilient cover.

10. The stethoscope recited in claim 9 wherein the cylindrical portion of the insert extends sufficiently beyond the resilient cover to contact the skin area to be monitored and to facilitate removal of the insert by hand.

11. A one-piece, deformable and resilient stethoscope bell insert comprising:
    a. an upper portion including a cylindrically-shaped outer wall, a curved inner wall and a rim connecting the outer wall to the inner wall, said rim being adapted to form an acoustic seal between the skin of a patient and the insert when the insert is contacted with the skin of the patient;
    b. a lower portion (1) connected to the upper portion, (2) including a bell-shaped outer wall and a curved inner wall connected to the inner wall of the upper portion whereby a continuous, sound-carrying, bell-shaped interior surface is formed within the insert and (3) having a central aperture therein whereat the outer and inner walls of the lower portion are tapered to meet; and
    c. a continuous, circumferential ridge connecting the outer wall of the upper portion with the outer wall of the lower portion.

12. The insert recited in claim 11 wherein the ridge comprises:
    a. a concave-shaped portion connecting the cylindrically-shaped outer wall of the upper portion with the ridge; and
    b. a convex-shaped portion connecting the bell-shaped outer wall of the lower portion with the ridge.

* * * * *